Figure 1:
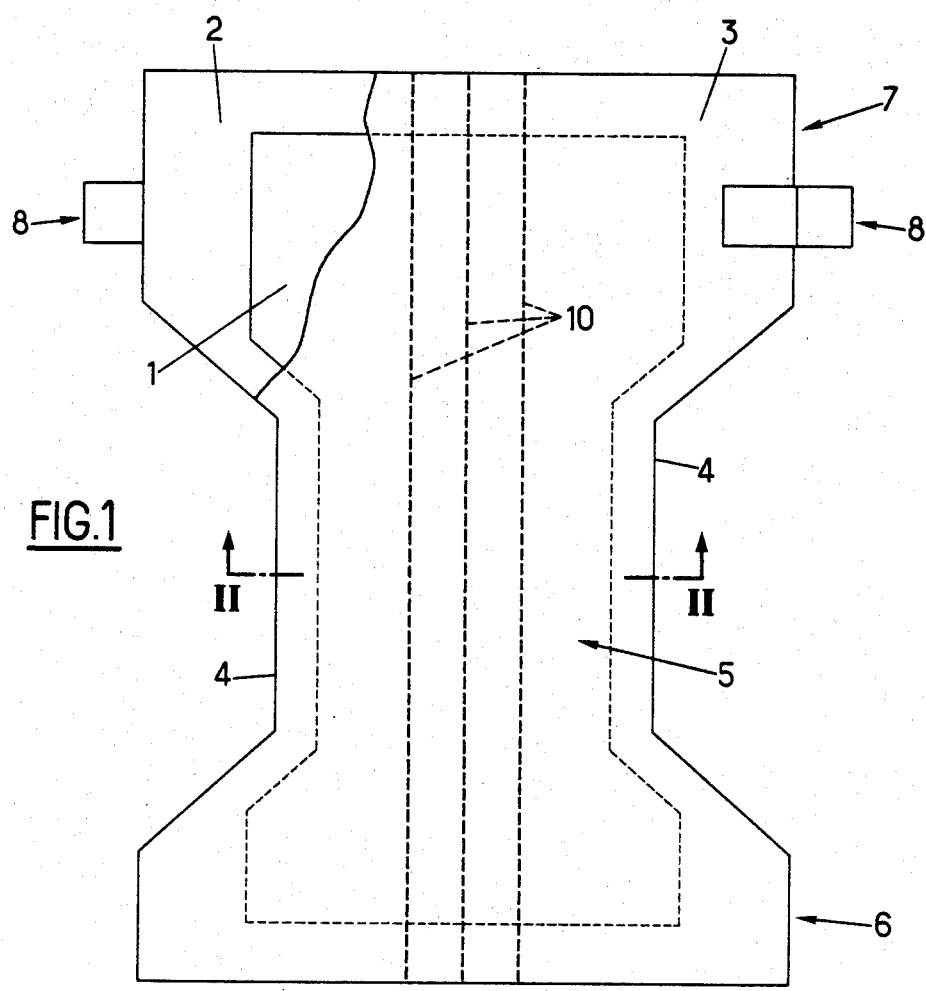

United States Patent [19]

De Jonckheere et al.

[11] Patent Number: 4,534,769
[45] Date of Patent: Aug. 13, 1985

[54] DIAPER

[75] Inventors: Raphael De Jonckheere, Bondues; Jacques Dussaud, La Madeleine, both of France

[73] Assignee: Boussac Saint Freres B.S.F., Lille, France

[21] Appl. No.: 504,413

[22] Filed: Jun. 15, 1983

[30] Foreign Application Priority Data

Jun. 24, 1982 [FR] France .............. 82 11107

[51] Int. Cl.³ .......................... A41B 13/02
[52] U.S. Cl. ............................... 604/369
[58] Field of Search .......... 604/369, 370, 367, 358, 604/385

[56] References Cited

U.S. PATENT DOCUMENTS

| 2,551,663 | 5/1951 | Fox ............................. | 128/290 |
| 3,916,900 | 11/1975 | Breyer et al. .................. | 128/287 |
| 4,041,949 | 8/1977 | Kozak ........................... | 128/287 |

FOREIGN PATENT DOCUMENTS

| 1441365 | 1/1969 | Fed. Rep. of Germany. |
| 1924813 | 11/1969 | Fed. Rep. of Germany. |
| 2178745 | 11/1973 | France. |
| 2355496 | 1/1978 | France. |

Primary Examiner—John D. Yasko
Attorney, Agent, or Firm—Owen, Wickersham & Erickson

[57] ABSTRACT

Diaper comprising an absorbent pad between a practically waterproof outer sheet and a water-permeable inner sheet.

The outer sheet (2) and the inner sheet (3) consist entirely of elastic materials, for example foams of plastics materials.

Application: notably to diapers for infants.

28 Claims, 2 Drawing Figures

DIAPER

This invention relates to a diaper, notably for infants, comprising a virtually waterproof outer envelope, an inner water-permeable sheet and an absorbent pad placed between the said outer envelope and the said inner sheet.

In known diapers both the outer envelope and the inner sheet are made up of non-elastic materials, for example one is a polyethylene sheet and the other a non-woven fabric. Provision has already been made on these known diapers for fitting elastics at the waist and at the leg openings. The waist elastics are designed to provide a better fit for the diaper. The leg opening elastics are designed to improve the diaper seal at these critical positions.

These separately fitted elastics do not, however, give complete satisfaction, and fitting them makes diaper manufacture considerably more complicated. Indeed, in addition to the excessive grip these elastics may have, they are positioned only on the margins of the diaper and frequently lead to ugly bulges in the remaining parts of the diaper. Furthermore the efficiency of these separately fitted elastics depends to a great extent on the accuracy with which the diaper is fitted on the infant, which requires a skill that can only be gained, in the most favourable case, after a certain time.

The object of the present invention is a diaper which, though being simpler to manufacture than diapers with fitted elastics, provides both a perfect fit and a good seal without producing unsightly bulging and without requiring the precision needed by known diapers in order to be correctly fitted on the infant.

In the diaper according to the invention the outer envelope and the inner sheet, which have the absorbent pad placed between them, are made up entirely of inherently elastic materials.

Because of this the materials making up the outer envelope and the inner sheet themselves fulfil the functions of the fitted elastics on the known diapers, i.e. the functions of gripping at the waist and leg openings, at the same time as avoiding unslightly bulging at the outer positions because of the integral elasticity of the outer envelope and the inner sheet.

Preferably the outer envelope and the inner sheet consist of elastic foams made of plastics materials.

At least the inner sheet is advantageously formed by a plastics material foam which is at least partly reticulated. Thus, reticulation of the foam makes the foam bubbles burst which gives the foam its permeability.

Preferably the outer envelope also consists of a foam which is at least partly reticulated.

Therefore, through the degree of reticulation, it is possible to choose the permeability of these foams both with respect to water and to air.

Another possibility for choosing the permeability of the outer envelope and inner sheet, notably when they are made of plastics material foam, preferably at least partially reticulated, consists in using the thickness of this envelope and this sheet. In particular it is thus possible to make the outer sheet so thick that it is watertight but permeable to air.

Of course it is possible to apply both the degree of reticulation of the foam and thickness to give the outer envelope and the inner sheet the required watertightness and air permeability.

If the same plastics material foam is used for the outer envelope and the inner sheet it is advantageous to give the outer sheet a thickness of between 1 and 5 mm, preferably between 2 and 4 mm, and the inner sheet a thickness of between 0.5 and 1.5 mm, preferably between 0.8 and 1.2 mm.

Polyurethane foam and polyester foam have, for example, given excellent results.

Preferably the outer envelope and the inner sheet are joined by a peripheral weld or adhesion line.

The absorbent pad, which is not generally elastic, is advantageously fixed, in the middle only of the width of the diaper, by one or more longitudinal adhesion lines, to the outer envelope and to the inner sheet. The outer envelope and the inner sheet thus retain their transverse elasticity, notably at belt level.

Figure 2:
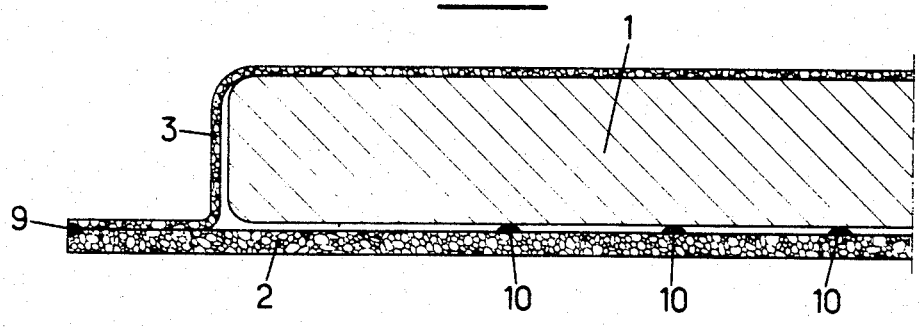

With reference being made to the appended drawing we shall describe in greater detail an illustrative non-restrictive embodiment of a diaper according to the invention: in the drawing:

FIG. 1 is a plan view of a diaper opened out flat;
FIG. 2 is a part section view along II—II of FIG. 1.

The diaper illustrated in the drawing comprises, in a known manner, an absorbent pad 1 placed between an outer sheet 2 and an inner sheet 3. The two sheets 2 and 3 are roughly rectangular in overall shaped and have two side cut-outs 4 on opposite sides.

The absorbent pad 1 has a corresponding shape and is slightly smaller than sheets 2 and 3, so that its edges are a little way back from the edge of sheets 2 and 3 round the whole periphery.

The diaper as shown above is used in a manner known per se such that the reduced-width middle crotch part 5 bounded by the two opposite side cut-outs 4, is placed between the infant's legs, that one of the wider end portions or front portion 6 is folded up onto the infant's abdomen and that the other wider end portion or back portion 7 is folded up onto the infant's posterior. An adhesive closure device 8 of a type known per se, fixed on the two side margins of the back portion 7, enables the diaper to be closed round the infant level, with each of the closure devices 8 being stuck onto the front portion 6.

According to the present invention the two sheets 2 and 3, instead of consisting, as is usually the case, of a flexible non-elastic sheet of waterproof plastics material for the first and of, for example, a flexible, but non-elastic, water-permeable non-woven fabric for the second, are both made from inherently elastic materials, preferably from plastics material foams. The two sheets 2 and 3 may consists of the same material foam, preferably a plastics material foam which is at least partly reticulated, i.e. a foam in which at least part of the bubbles are burst open. So that, in this case, the inner sheet 3 is both water- and air-permeable and so that the outer sheet 2 is waterproof, but preferably permeable to air, the inner sheet 3 is made significantly less thick than the outer sheet 2. To give an example, in the case of using the same polyurethane foam for both sheets 2 and 3, it is possible to give the inner sheet 3 a thickness of between 0.5 and 1.5 mm and the outer sheet a thickness of between 1 and 5 mm.

The two sheets 2 and 3 are connected together at their edge and over their whole periphery by a weld line 9 (FIG. 2).

The absorbent pad 1, which may have any structure (cellulose or other absorbent product), is fixed, when it is not itself elastic, to the outer sheet 2 by two lines of adhesive 10 in the middle of the diaper width only. These fixing lines 10 are only designed to hold the pad 1, without appreciably reducing the transverse elasticity of sheets 2 and 3 at the level of the diaper waist.

It goes without saying that the invention, which consists in using elastic materials for the outer sheet and the inner sheet of a diaper, an absorbent pad being placed between these sheets, is applicable to all types of diapers, i.e. both to open diapers like the one shown and to closed diapers forming briefs.

Further, instead of using the same plastics material foam for both sheets and giving these sheets different thicknesses so that one is permeable to water and the other is waterproof, it would also be possible to use different foams having different degrees of reticulation for the two sheets, or even to combine the two measures (thickness and degree of reticulation) that can be used to influence permeablity.

Furthermore, the two sheets could also consist of other elastic materials apart from plastics material foams.

Actual manufacture of the diaper can be carried out using known processes, preferably processes applying two continuous strips in which the sheet pieces forming the various diapers are cut longwise or transversally after the absorbent pads have been installed between the strips.

We claim;

1. A diaper, especially for infants, comprising
   an outer sheet of plastic foam which is elastic and air-permeable but water-impermeable,
   an inner sheet of plastic foam which is elastic, air-permeable, and water-permeable,
   a water absorbent pad located between said outer sheet and said inner sheet, and
   fastening means fixed on two opposite side margins of the diaper in order to close the diaper around the waist of the infant.

2. The diaper according to claim 1 wherein said plastic foams are at least partially reticulated.

3. The diaper according to claim 1 wherein the outer sheet is thicker than the inner sheet.

4. The diaper according to claim 3 wherein the outer sheet has a thickness of between 1 and 5 mm., and the inner sheet has a thickness of between 0.5 and 1.5 mm.

5. The diaper according to claim 4 wherein the thickness of the outer sheet lies between 2 and 4 mm. and the thickness of the inner sheet lies between 0.8 and 1.2 mm.

6. The diaper according to claim 1 wherein the foam of the outer sheet is less reticulated than that of the inner sheet.

7. The diaper according to claim 1 wherein the outer and inner sheets are affixed together by a peripheral weld adhesion line.

8. The diaper according to claim 1 wherein the absorbent pad is affixed to one said sheet in the middle of the diaper width only, by at least one longitudinal adhesion line.

9. The diaper according to claim 1 wherein the outer and inner sheets are polyurethane or polyester foam.

10. A diaper, especially for infants, comprising
    an outer sheet of plastic foam which is elastic and air-permeable but water-impermeable and is at least partially reticulated,
    an inner sheet of plastic foam which is elastic and air-permeable and water-permeable and is at least partially reticulated,
    a water absorbent pad located between said outer sheet and said inner sheet, and
    fastening means fixed on two opposite side margins of the diaper in order to close the diaper around the waist of the infant.

11. The diaper according to claim 10 wherein the outer sheet is thicker than the inner sheet.

12. The diaper according to claim 11 wherein the outer sheet has a thickness of between 1 and 5 mm., and the inner sheet has a thickness of between 0.5 and 1.5 mm.

13. The diaper according to claim 12 wherein the thickness of the outer sheet is between 2 and 4 mm. and the thickness of the inner sheet is between 0.8 and 1.2 mm.

14. The diaper according to claim 10 wherein the foam of the outer sheet is less reticulated than that of the inner sheet.

15. The diaper according to claim 10 wherein the outer and inner sheets are affixed together by a peripheral weld or adhesion line.

16. The diaper according to claim 10 wherein the absorbent pad is affixed to one said sheet, in the middle of the diaper width only, by at least on longitudinal adhesion line.

17. The diaper according to claim 10 wherein the outer and inner sheets are polyurethane or polyester foam.

18. A diaper especially for infants, comprising
    an outer sheet,
    an inner sheet,
    a water absorbent pad in between said outer sheet and said inner sheet, and
    fastening means fixed on two opposite side margins of the diaper in order to close the diaper around the waist of the infant,
    the outer sheet and the inner sheet each being made of a first and a second layer of the same elastic plastic foam material, which is at least partially reticulated, said second layer being thicker than said first layer, so that said outer sheet is air-permeable but water-impermeable and said inner sheet is both air-permeable and water-permeable.

19. The diaper according to claim 18 wherein the outer sheet has a thickness of between 1 and 5 mm., and the inner sheet has a thickness of between 0.5 and 1.5 mm.

20. The diaper according to claim 19 wherein the outer sheet is between 2 and 4 mm. thick and the inner sheet is between 0.8 and 1.2 mm. thick.

21. The diaper according to claim 18 wherein the foam of the outer sheet is less reticulated than that of the inner sheet.

22. The diaper according to claim 18 wherein the outer and inner sheets are fixed together by a peripheral weld or adhesion line.

23. The diaper according to claim 18 wherein the absorbent pad is affixed to one said sheet, in the middle of the diaper width only, by one or more longitudinal adhesion lines.

24. The diaper according to claim 18 wherein the outer and inner sheets are polyurethane or polyester foam.

25. A diaper, especially for infants, comprising
    an outer sheet,
    an inner sheet,
    a water absorbent pad located between said outer sheet and said inner sheet, and fastening means fixed on two opposite side margins of the diaper in order to close the diaper around the waist of the infant, wherein said outer sheet and said inner sheet are each made of a first and a second layer of an elastic foam of partially reticulated plastics material, the foam of said first layer being less reticulated than the foam of said second layer, so that said outer sheet is air-permeable but water-impermeable while said inner sheet is both air-permeable and water-permeable.

26. The diaper according to claim 25 wherein the outer and inner sheets are affixed together by a peripheral weld or adhesion line.

27. The diaper according to claim 25 wherein the absorbent pad is affixed to one said sheet, in the middle of the diaper width only, by one or more longitudinal adhesion lines.

28. The diaper according to claim 25 wherein the outer and inner sheets are polyurethane or polyester foam.

* * * * *

UNITED STATES PATENT AND TRADEMARK OFFICE
CERTIFICATE OF CORRECTION

PATENT NO. : 4,534,769
DATED : August 13, 1985
INVENTOR(S) : Raphael De Jonckheere and Jacques Dussaud It is certified that error appears in the above-identified patent and that said Letters Patent are hereby corrected as shown below:

Column 1, line 45, "outer" should read --other--.
Column 1, line 66, before "thickness" insert --the--.
Column 2, line 26, "shaped" should read --shape--.
Column 2, line 41, after "infant" insert --at belt--.
Column 2, line 51, "consists" should read --consist--.
Column 2, line 51, before "material" insert --plastics--.
Column 3, line 15, after "foams" insert --or foams--.
Column 4, line 24, "on" should read --one--.

Signed and Sealed this

Twelfth Day of November 1985

[SEAL]

Attest:

Attesting Officer

DONALD J. QUIGG

Commissioner of Patents and Trademarks